US008349279B2

(12) United States Patent
Taike et al.

(10) Patent No.: US 8,349,279 B2
(45) Date of Patent: Jan. 8, 2013

(54) SAMPLES STORAGE SYSTEM FOR PHARMACEUTICAL DEVELOPMENT

(75) Inventors: Hiroyuki Taike, Osaka (JP); Kazuhiro Tsutsumi, Osaka (JP); Hisao Nishii, Osaka (JP); Nobuaki Matsumoto, Osaka (JP); Yukio Ueyama, Kobe (JP)

(73) Assignee: Tsubakimoto Chain Co., Osaka (JP)

( * ) Notice: Subject to any disclaimer, the term of this patent is extended or adjusted under 35 U.S.C. 154(b) by 173 days.

(21) Appl. No.: 12/837,844

(22) Filed: Jul. 16, 2010

(65) Prior Publication Data

US 2010/0294734 A1 Nov. 25, 2010

Related U.S. Application Data

(63) Continuation-in-part of application No. 11/473,294, filed on Jun. 22, 2006, now Pat. No. 7,892,504, and a continuation-in-part of application No. 11/710,160, filed on Feb. 23, 2007, now abandoned.

(30) Foreign Application Priority Data

Jul. 22, 2005 (JP) ................................ 2005-212690
May 1, 2006 (JP) ................................ 2006-127835

(51) Int. Cl.

| | |
|---|---|
| ***B01L 3/00*** | (2006.01) |
| ***B01L 9/00*** | (2006.01) |
| ***B01L 9/06*** | (2006.01) |
| *A47F 7/00* | (2006.01) |
| *B65D 1/34* | (2006.01) |
| *C12M 3/00* | (2006.01) |

(52) U.S. Cl. ........ 422/552; 422/553; 422/561; 422/562; 435/288.1; 435/288.2; 435/288.3; 435/288.4; 435/305.2; 206/561; 211/85.13; 211/13.1

(58) Field of Classification Search .................. 422/552; 211/85.13

See application file for complete search history.

(56) References Cited

U.S. PATENT DOCUMENTS

| | | | | |
|---|---|---|---|---|
| 4,154,795 | A * | 5/1979 | Thorne | 422/553 |
| 6,878,341 | B2 * | 4/2005 | Kowallis et al. | 422/63 |
| 7,018,588 | B2 * | 3/2006 | DeSilets et al. | 422/534 |
| 7,128,878 | B2 * | 10/2006 | Muser | 422/552 |

FOREIGN PATENT DOCUMENTS

| | | |
|---|---|---|
| EP | 1477226 A1 * | 11/2004 |
| JP | 43-4518 | 2/1968 |
| JP | 03-059200 | 10/1992 |

OTHER PUBLICATIONS

Office Action dated Aug. 10, 2010 with translation of JP Application 2006-127835.

* cited by examiner

*Primary Examiner* — Dennis M White
*Assistant Examiner* — Jennifer Wecker
(74) *Attorney, Agent, or Firm* — Dann, Dorfman, Herrell & Skillman; Henry H. Skillman

(57) ABSTRACT

A samples storage system for pharmaceutical development in which the usable volumes of ultramicrotubes (384 tubes) are increased and smooth insertion and extraction of ultramicrotubes is possible irrespective of the positions of the ultramicrotubes. The samples storage system includes tubes in which samples are sealed and a storage rack for vertically accommodating a plurality of the tubes in a grid pattern. Each tube is of a rectangular hollow tubular cross-section and the intersect is tapered toward the bottom portion of the tube. Corner portions of the outer four side surfaces of the tubes are chamfered. The storage rack has engagement partition walls forming open-ended sections in a grid pattern inside the rack frame. The height of the walls is smaller than the length of the tube, and tube-supporting pins project vertically from the intersections of the grid. The outermost walls of the grid are spaced inwardly from the frame so that all of the tubes in the grid are supported for ready insertion and removal.

3 Claims, 6 Drawing Sheets

SAMPLES STORAGE SYSTEM FOR PHARMACEUTICAL DEVELOPMENT

RELATED APPLICATIONS

The present application is a continuation-in-part of U.S. patent application Ser. Nos. 11/473,294 filed Jun. 22, 2006, now U.S. Pat. No. 7,892,504 and 11/710,160 filed Feb. 23, 2007, now abandoned the disclosures of which are incorporated herein by reference.

FIELD OF THE INVENTION

The present invention relates to a samples storage system for pharmaceutical development used for identifying and storing a number of samples in a field of a pharmaceutical development research or the like, and more specifically it relates to a samples storage system for pharmaceutical development including tubes for sealing samples for pharmaceutical development and a storage rack for vertically accommodating 384 tubes in a grid pattern, of the type shown in U.S. patent application Ser. No. 11/473,294 (Published Application No. US 2007/0017885 A1).

BACKGROUND OF THE INVENTION

In a field of wound medicine research or the like, the storage and transportation of samples has been carried out by sealing or encapsulating a sample-dissolved solution into a tube case so called as a microtube and accommodating a plurality of microtubes in a vertically provided manner in a storage rack which is partitioned in a grid pattern, for example partitioned into 96 receptacles in a matrix with 8 rows and 12 columns. Further, to accommodate smaller microtubes that is ultramicrotubes (hereinafter sometimes referred to as “384 tube”) in the same size storage rack as a storage rack partitioned into 96 sections in accordance with a standard of SBS (Society for Biomolecular Screening) a storage rack with the total of 384 partitioned sections in a matrix with 16 rows and 24 columns has been also known [(see for example, European Patent Application Publication No. 0904841 (FIG. 1, paragraphs 7 to 9) and European Patent Application Publication No. 1477226 (FIG. 5, paragraphs 3 to 5) and related U.S. Pat. No. 6,827,907].

FIG. 8 shows a samples storage system 800 for pharmaceutical development for accommodating ultramicrotubes (or 384 tubes) described in European Patent Application Publication No. 0904841. In this samples storage system 800 for pharmaceutical development, in a storage rack 810 with the same size as the storage rack in accordance with an SBS standard, in which 96 tubes are accommodated, it is four times number of tubes, that is 384, tubular ultramicrotubes 820 with bottoms are accommodated. Thus since the above-mentioned ultramicrotubes 820 take a shape in which a bottom surface size of a the ultramicrotubes (384 tubes) was reduced to substantially ¼ of the surface size of the microtubes (96 tubes), the capacity of samples to be accommodated must be decreased. Further, since engagement partition walls 816 for forming accommodation sections 813 partitioned in a matrix with 16 rows and 24 columns are formed at substantially the same height as a rack frame 814 of the storage rack 810, an accommodation region in the ultramicrotubes 820 is decreased by the thickness of these engagement partition walls 816 and the capacity of samples to be accommodated was even more restricted as compared with the microtubes (96 tubes).

FIG. 9 shows a partial cross-sectional view of a samples storage system 900 for pharmaceutical development accommodating ultramicrotubes described in European Patent Application Publication No. 1477226. In this samples storage system 900 for pharmaceutical development, a storage rack 910 accommodates four times number of tubes, that is ultramicrotubes 920, is the same size storage rack 910 as a storage rack in accordance with the SBS standard, accommodating microtubes (96 tubes) like the conventional case shown in FIG. 8. Since the ultramicrotubes 920 in this storage rack 910 have a rectangular hollow tubular cross-section, the storage rack 910 has a greater accommodation volume than the tubular ultramicrotubes shown in FIG. 8.

However, since in this storage rack 910, engagement partition walls 916 extend to shoulder portions 922 of ultramicrotubes 920 and corner portions of the outer surfaces of the ultramicrotubes have chamfered portions (not shown), slight gaps are formed at corner portions of an accommodation portion 913 whose top are a square, resulting in a reduced increase in the accommodation volume by reason of the gaps. Further, since one surface or two surfaces of the respective tubes 920 accommodated adjacent the frame are supported against frame side walls 918, which are unlikely to elastically deform, the tubes 920 are difficult to insert and extract. Further, since there are differences in forces required for insertion and extraction between a case of tubes at the center portion of the storage rack and a case of tubes near the rack side wall 918, a complex control is required when picking with an automatic picking device.

SUMMARY OF THE INVENTION

Accordingly, the object of the present invention is to provide a samples storage system for pharmaceutical development in which the accommodation volumes of ultramicrotubes are increased and smooth insertion and extraction of ultramicrotubes become possible irrespective of the accommodation positions of the ultramicrotubes relative to the side walls.

Means for Solving the Problems

The invention attains the above-mentioned object by a samples storage system for pharmaceutical development including tubes in which samples for pharmaceutical development are sealed and a storage rack with receptacles for vertically accommodating a plurality of the tubes in a grid pattern, characterized in that the tube is of a rectangular hollow tubular cross-section and has a reduced outer perimeter toward the bottom portion of the tube and at the same time corner portions of the outer four side surfaces of the tubes are chamfered, the storage rack has engagement partition walls forming grid pattern receptacles inside the rack frame. The height of the walls is smaller than the length of the tube. The grid partition walls have tube-supporting pins vertically extending from their respective intersections of the grid. The tubes accommodated adjacent the outermost sides are held vertical by the partition walls which are spaced from the frame and the tube-supporting pins projecting upwardly from the intersections of the grid in the same manner as the tubes in the middle of the rack.

The material of the tube and the rack used in the present invention is not limited particularly, but polypropylene (PP) or polycarbonate (PC) is preferably used as the material.

Effects of the Invention

According to the invention, since in a samples storage system for pharmaceutical development including tubes in which samples for pharmaceutical development are sealed and a storage rack for accommodating a plurality of the vertical tubes in a grid pattern, the tube is of a rectangular hollow tubular cross-section and has a reduced outer perimeter toward the bottom portion of the tube and at the same time corner portions of the outer four side surfaces of the tubes are chamfered. The storage rack has engagement partition walls forming grid pattern receptacles inside the rack frame. The height of the walls is smaller than the length of the tube, and the grid partition walls have tube-supporting pins extending vertically from the respective intersections of the grid. The tubes accommodated on the sides adjacent the frame are held by the partition walls and tube-supporting pins vertically provided on the intersections of the grid as in other tubes, the accommodation volume of tubes can be increased and smooth insertion and extraction of tubes become possible irrespective of the accommodation positions of the tubes. Thus the beneficial effects are very large.

PREFERRED EMBODIMENT OF THE INVENTION

Figure 1:
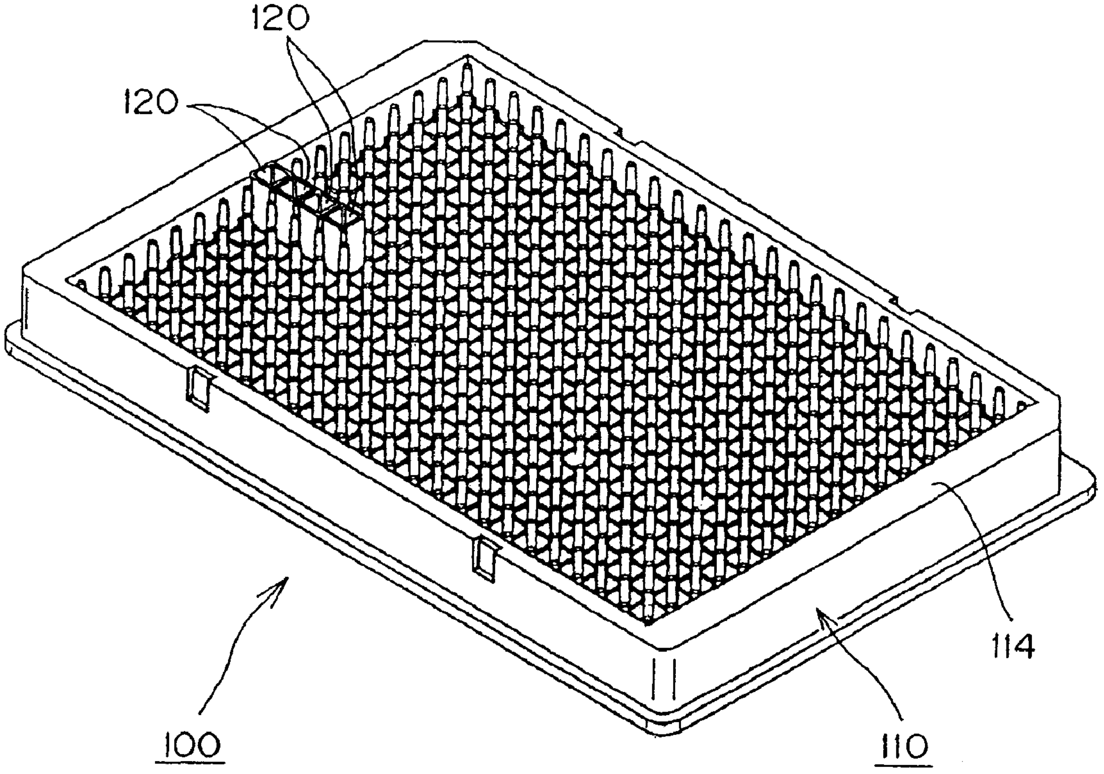
FIG. 1 is a perspective view of a samples storage system for pharmaceutical development according to the present invention.
Figure 2:
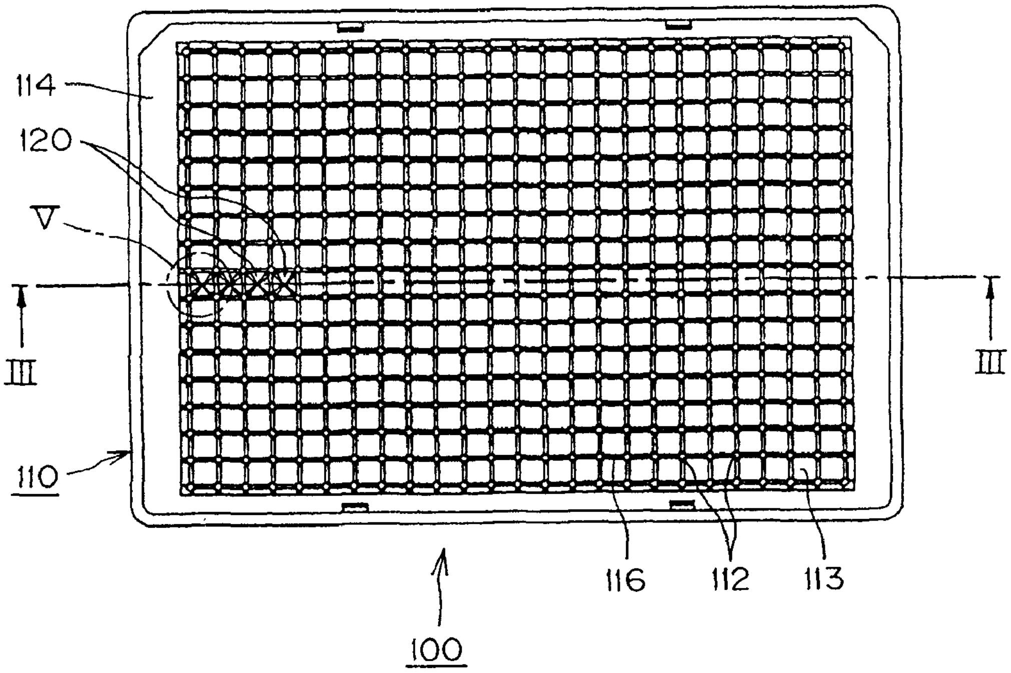
FIG. 2 is top view of a storage rack shown in FIG. 1.
Figure 3:
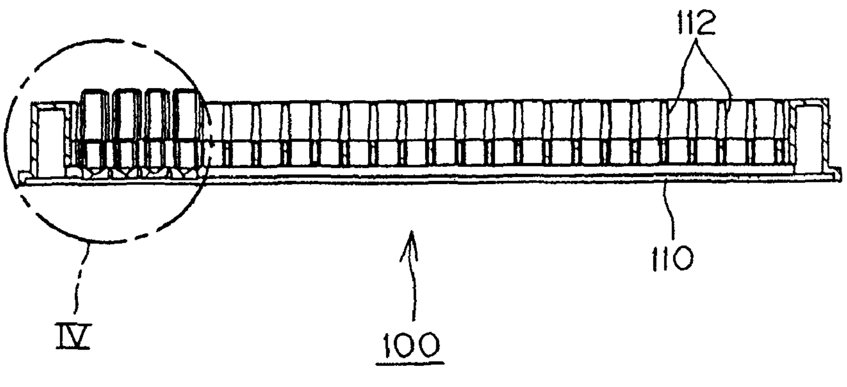
FIG. 3 is a cross-sectional view taken along the line III-III of the storage rack shown in FIG. 2.

Next, a preferable example of a samples storage system for pharmaceutical development according to the present invention will be described with reference to drawings.

In the drawings, four ultramicrotubes 120 are accommodated in a storage rack 110. The storage rack 110, which is one of components of a samples storage system for pharmaceutical development of the present invention, has a hollow rack frame 114 and lower engagement partition walls 116 forming grid pattern of open-ended receptacles inside the rack frame. It is noted that the outermost partition walls 116, which are adjacent the rack frame, are spaced inwardly of the inside of the inner frame walls 118 of the hollow rack frame 114, and the height of all of the partition walls 116 is less than the length of the associated ultramicrotubes. Tube-supporting pins 112 extend vertically upwardly from the respective intersections of the grid.

Figure 4:
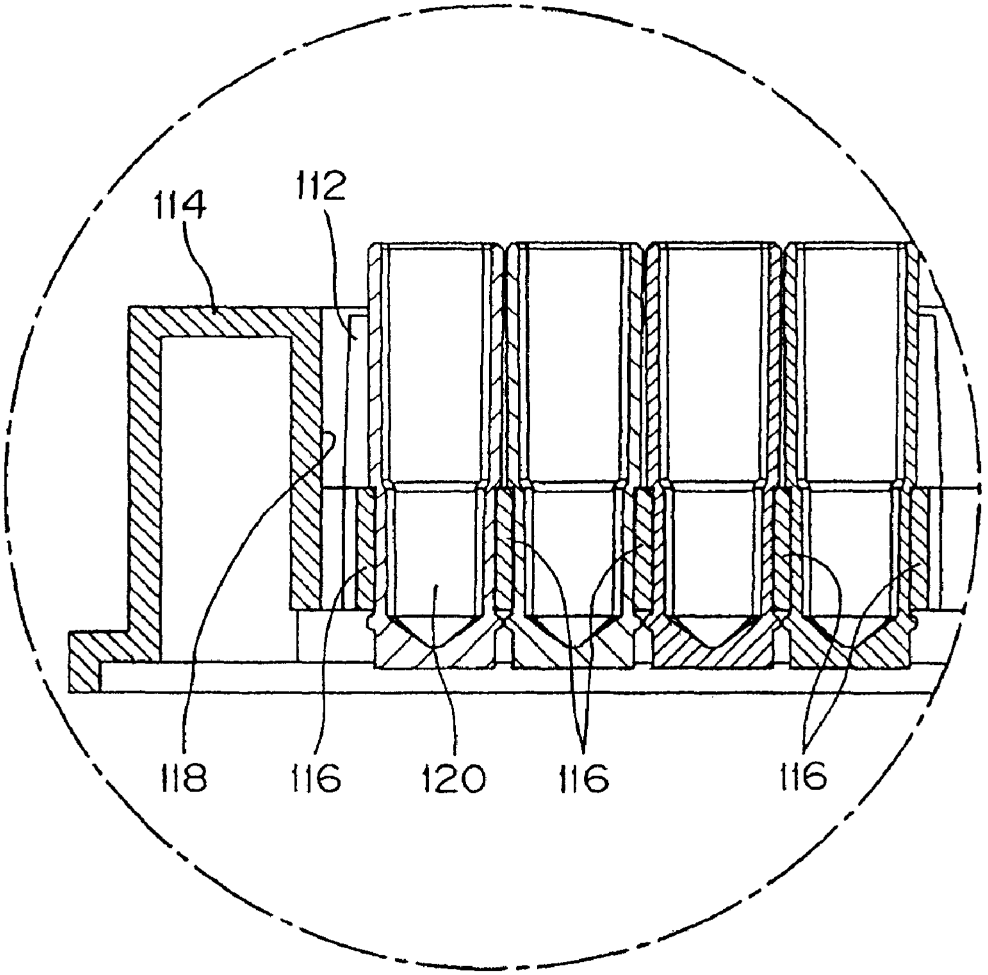
FIG. 4 is an enlarged view of the portion encircled at IV in FIG. 3.
Figure 5:
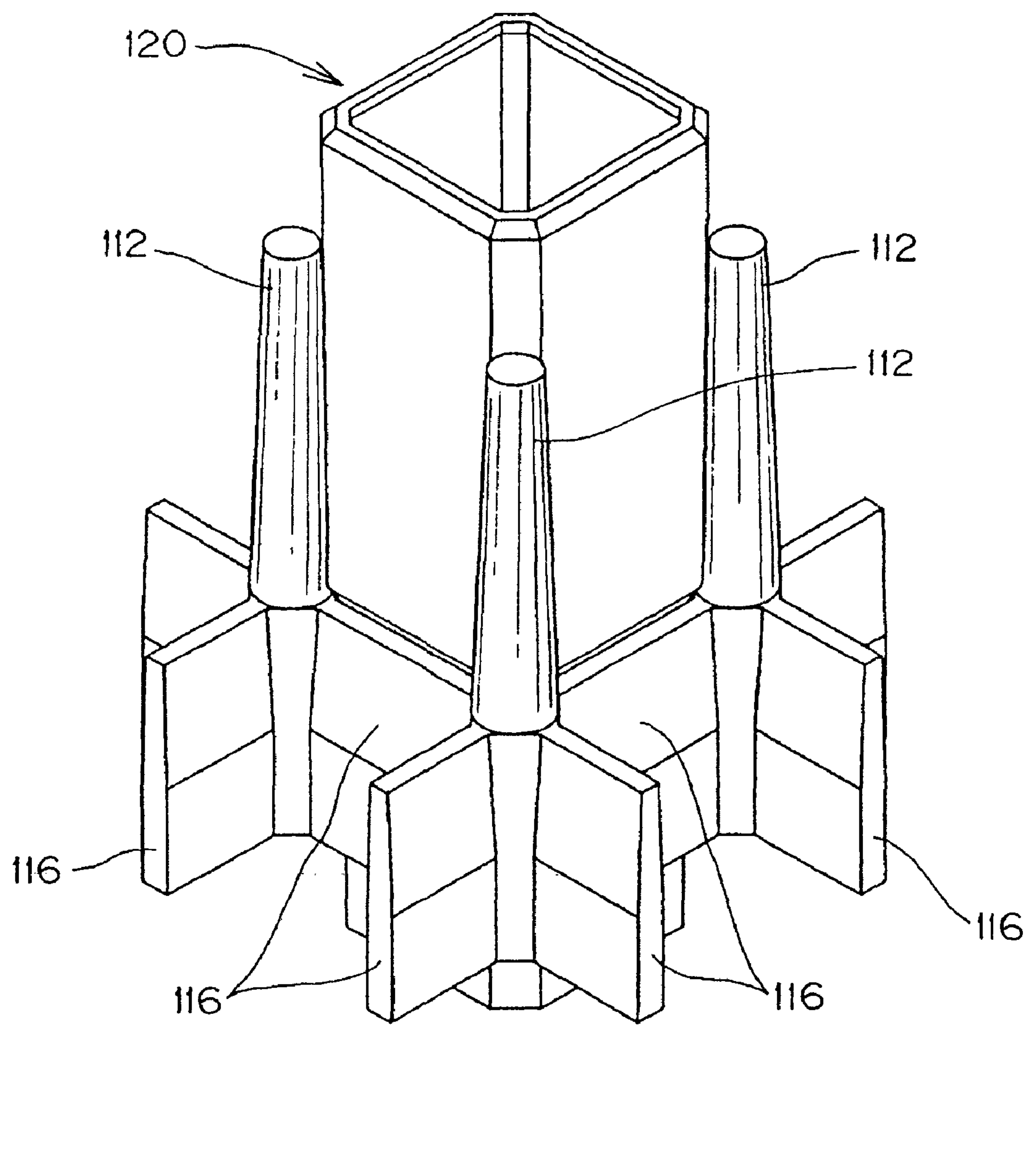
FIG. 5 is an enlarged perspective view of the portion encircled at V in FIG. 2.
Figure 7:
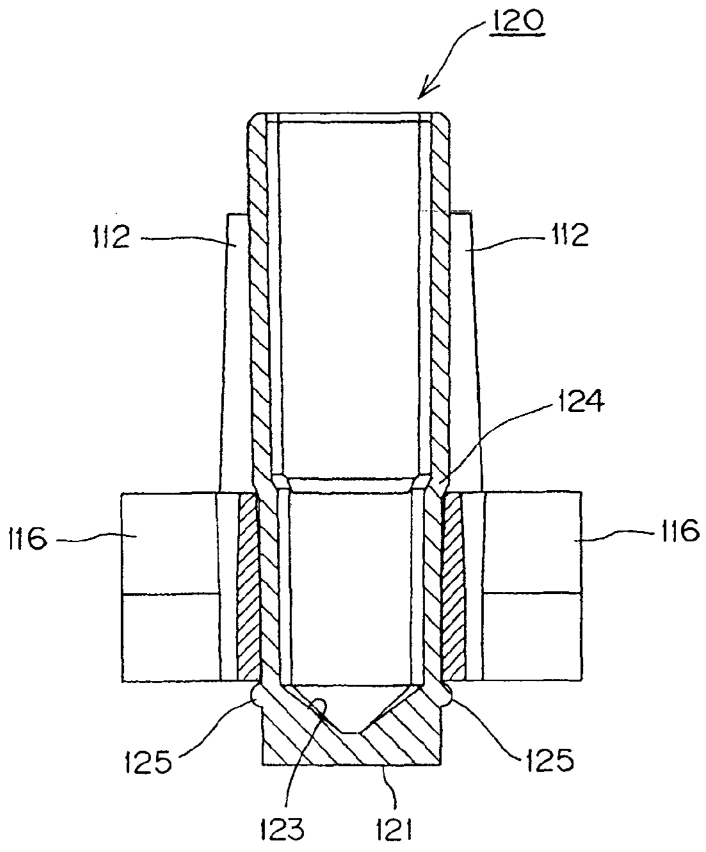
FIG. 7 is a cross-sectional view taken along the line VII-VII in FIG. 6.
Figure 8:
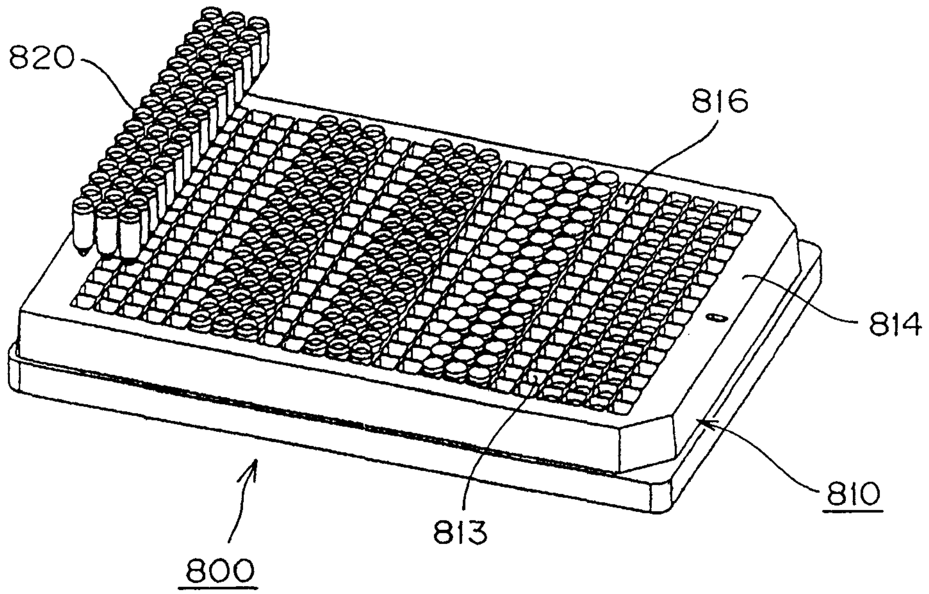
Fig. 8 Prior Art
FIG. 8 is a perspective view of conventional ultramicrotubes and a conventional storage rack.

As shown in FIGS. 5 and 7, the pins 112 taper upwardly from the intersections to guide the ultramicrotubes into the receptacles when loading the rack, and the ultramicrotubes do not come into contact with the rack frame wall 118, and as shown in FIGS. 4 and 5, the outermost side ultramicrotube 120 is held, like other ultramicrotubes, by lower engagement partition walls 116 forming grid pattern sections inside than the length of the respective ultramicrotubes and four tube supporting pins 112 vertically upwardly provided from the respective intersections of the grid of the engagement partition walls 116. Therefore, the outermost side ultramicrotube 120 does not come into contact with a rack frame side wall 118.

Figure 6:
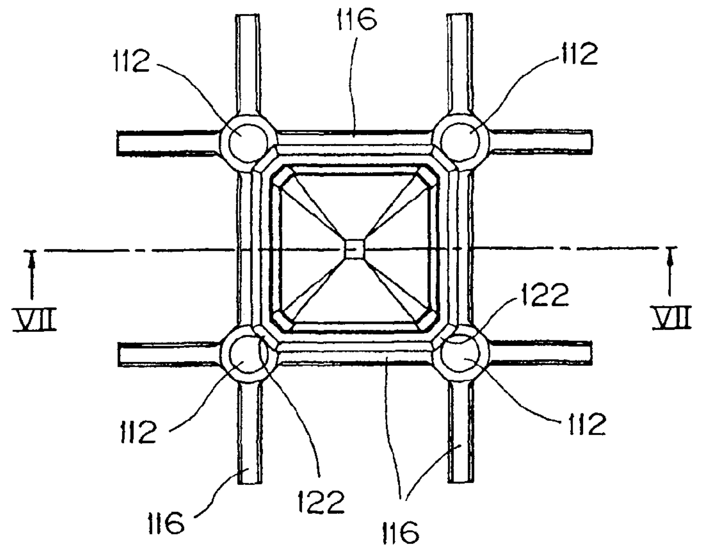
FIG. 6 is a top view of an ultramicrotube and a storage rack of the present invention shown in FIG. 5.

As apparent from FIGS. 6 and 7, the ultramicrotube 120 has a rectangular hollow tubular cross-section and has a reduced outer perimeter toward a bottom surface 121 and corner portions on the outer four side surfaces of the ultramicrotube 120 are chamfered, as indicated at 122 in FIG. 6. The ultramicrotube 120 has step portions 124 forming a shoulder at positions where the ultramicrotube 120 abuts on upper surfaces of the engagement partition walls 116, and this shoulder prevents the ultramicrotube 120 from slipping down past the upper surfaces of the engagement partition walls 116. Although the outer bottom surface of the ultramicrotube 120 is flat, the inner bottom surface 123 of the ultramicrotube 120 has inclined surfaces toward the center of the inner bottom, like a square pyramid. This shape makes the residues of solution extremely small when the solution in the ultramicrotube 120 is extracted by a pipet or the like.

Further, as shown in FIG. 7, tube locking convex projections 125 are provided on the respective outer four side surfaces at a lower portion of the ultramicrotube 120. When the ultramicrotube 120 is being inserted into an accommodation portion 113, which is one of sections of a grid pattern surrounded by four engagement partition walls 116, the tube locking convex projection 125 comes into contact with the upper surfaces of the engagement partition walls 116. One or both of the engagement partition walls 116 and the tube locking convex projections 125 are elastically deformed so that the tube locking convex projections 125 are slipped down below the engagement partition walls 116. It is noted that since the outermost partition wall 116 is spaced from the frame side wall 118, the partition wall 116 is free to deflect, which enables the projection 125 to pass through the receptacle. Although not illustrated herein, the tube-locking projections may be formed on the partition wall, and the lower portion of the microtube may have concavities to receive the projections and lock the tubes in the accommodation portion of the rack by elastic deformation.

Figure 9:
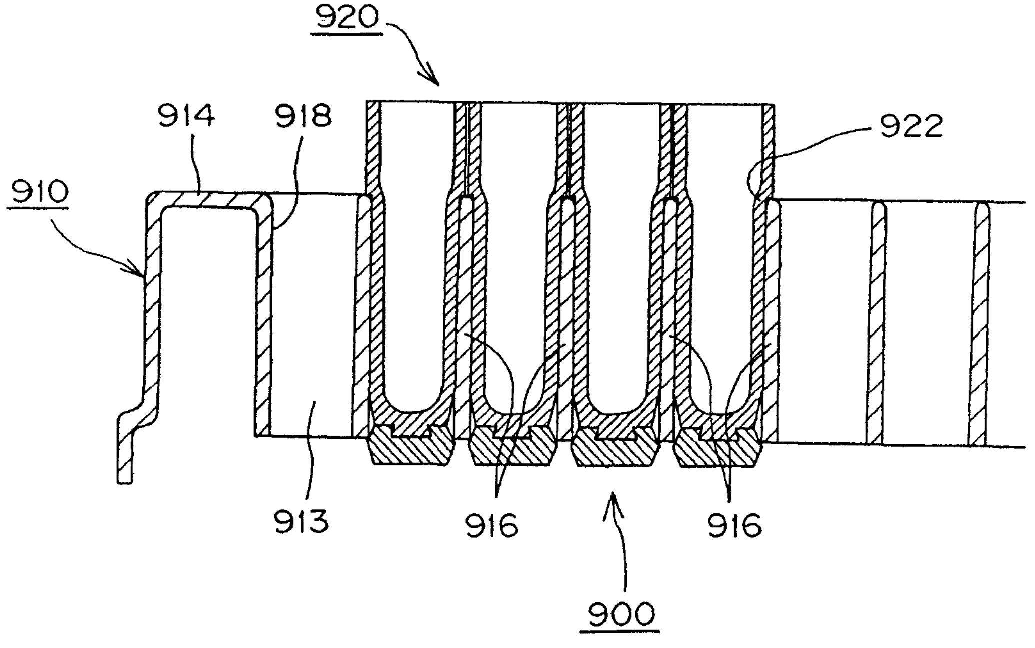
Fig. 9 Prior Art
FIG. 9 is a part of a cross-sectional view of other conventional ultramicrotubes and a storage rack.

At this time since the engagement partition walls 116 and the tube locking convex projections 125 come into point contact with each other and the height of the engagement partition wall 116 is smaller than the length of the ultramicrotube 120, the ultramicrotube 120 can be inserted into the storage rack 110 by smaller force as compared with the conventional storage rack 910 for tubes shown in FIG. 9 for example. Further, once the tube locking convex projections 125 are slipped down below the engagement partition walls 116, even if vibration is applied to the storage rack 110, the ultramicrotube 120 does not come out of the storage rack 110. When a specified ultramicrotube 120 accommodated in the storage rack 110 is pulled out through the top of the rack, it can be easily pulled out by sticking a probe against the bottom of the tube through the lower side of the storage rack 110. In the event it is desired to extract the microtube through the bottom of the rack, the step portions 124 on the microtube may be replaced by convex projections similar to the projections 125.

In the above-mentioned example, an embodiment has been disclosed in which the tube locking convex projections are provided on four side surfaces of the lower portion of the ultramicrotubes 120 at the same distance from the bottom surface of the ultramicrotube 120. However, various examples of numbers, sizes and distances from the bottom and the like of the tube locking convex projections are considered.

The invention claimed is:

1. A samples storage system for pharmaceutical development including tubes in which samples for pharmaceutical development are sealed and a storage rack for vertically accommodating a plurality of said tubes in a grid pattern, characterized in that said tubes are of a rectangular hollow tubular cross-section which has a reduced outer perimeter toward the bottom portion of the tube and four sides with chamfered corner portions on the outer side surfaces, and said storage rack has a hollow frame with inner and outer walls, and engagement partition walls within said inner walls intersecting one another and forming grid pattern sections inside said rack frame, said partition walls having a height smaller than the length of said tubes and-cooperating to form open-ended receptacles for association with said tubes, the outermost engagement partition walls adjacent said frame being spaced from said frame inner walls to provide a partition-wall-receiving space, each said tube having a shoulder on its periphery in said side surfaces at the top of said reduced outer perimeter and a convex portion at the bottom of said reduced perimeter spaced a selected distance below said shoulder, said selected distance being not less than the height of said partition walls, and at least said outermost engagement partition walls being elastically deflectable into said partition-wall-receiving space and deformable to enable said shoulder and said convex portion to engage the top and bottom of said outermost engagement partition wall to effect releasable interlocking engagement of said tube in said open-ended receptacle, said engagement partition walls have tube supporting pins extending vertically from respective intersections of the engagement partition walls, whereby all of said tubes, including the tubes accommodated adjacent said frame are held by said engagement partition walls and said tube supporting pins.

2. A storage rack adapted for use in a system for pharmaceutical development having tubes in which samples for pharmaceutical development are sealed, said tubes having a rectangular hollow tubular cross-section which has a reduced outer perimeter toward the bottom portion of the tube and four sides with chamfered corner portions on the outer surfaces, said reduced perimeter having a shoulder at the top and a convex portion at the bottom, said storage rack having a hollow frame with inner and outer frame walls, and engagement partition walls within said inner frame walls, said engagement partition walls intersecting one another and forming grid pattern of open-ended receptacles inside said rack frame, said engagement partition walls having a height smaller than the length of said tubes, said engagement partition wall being elastically deformable to enable said shoulder and said convex portion to engage the top and bottom of said engagement partition wall to effect releasable interlocking engagement of said tube in said open-ended receptacle, the outermost of said engagement partition walls within said hollow frame being spaced from the inner walls of said frame to provide a partition-wall-receiving space, at least said outermost engagement partition walls being elastically deflectable into said partition-wall-receiving space and being deformable to enable said shoulder and said convex portion to engage the top and bottom of said outermost engagement partition wall to effect releasable interlocking engagement of said tube in said open-ended receptacle said engagement partition walls have tube supporting pins extending vertically from respective intersections of the engagement partition walls, whereby all of said tubes, including the tubes accommodated adjacent said frame are held by said engagement partition walls and said tube supporting pins.

3. A storage rack according to claim 2 wherein said pins are tapered upwardly to guide the tubes into said receptacles during insertion of the tubes into said receptacles.

* * * * *